US009753025B2

(12) United States Patent
Mullin

(10) Patent No.: US 9,753,025 B2
(45) Date of Patent: *Sep. 5, 2017

(54) MOBILE WIRELESS HAND-HELD IDENTIFICATION SYSTEM AND BREATHALYZER

(71) Applicant: BI2 Technologies, LLC, Plymouth, MA (US)

(72) Inventor: Sean Mullin, Manomet, MA (US)

(73) Assignee: BI2 TECHNOLOGIES, LLC, Plymouth, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/242,965

(22) Filed: Aug. 22, 2016

(65) Prior Publication Data

US 2016/0358029 A1 Dec. 8, 2016

Related U.S. Application Data

(63) Continuation-in-part of application No. 15/017,230, filed on Feb. 5, 2016, now Pat. No. 9,507,926, which
(Continued)

(51) Int. Cl.
*G06F 21/32* (2013.01)
*G06K 9/00* (2006.01)
(Continued)

(52) U.S. Cl.
CPC ....... *G01N 33/4972* (2013.01); *G06F 1/1626* (2013.01); *G06F 1/1632* (2013.01);
(Continued)

(58) Field of Classification Search
CPC ..................................................... G06F 21/32
(Continued)

(56) References Cited

U.S. PATENT DOCUMENTS 4,641,349 A 2/1987 Flomo et al.
5,291,560 A 3/1994 Daugman
(Continued)

FOREIGN PATENT DOCUMENTS

EP 1833002 A1 9/2007

OTHER PUBLICATIONS

Kang, Jin-Suk, "Mobile iris recognition systems: An emerging biometric technology", International Conference on Computational Science, ICCS 2010, Procedia Computer Science 1 (2010) 475-484, www.sciencedirect.com.
(Continued)

*Primary Examiner* — Alexander Lagor
(74) *Attorney, Agent, or Firm* — Barlow, Josephs & Holmes, Ltd.

(57) ABSTRACT

A mobile, wireless biometric identification system includes a biometric capture device which enables a smartphone, using a commercially established wireless communication networks, to capture a digital image of a human biometric (iris, fingerprint, etc.) for transmission to a central server. The biometric capture device captures a high quality image for encoding and comparison, while the overall system leverages the existing cellular communication network. The device includes at least one other data capture device which can read, capture and transmit at least one of a variety of other data types from a variety of different government issued credentials, such as passports, driver's licenses, etc. A breathalyzer module can capture of breathalyzer sample and combine the sample data with other captured identification data to positively link the sample to the individual providing the sample.

12 Claims, 11 Drawing Sheets

Related U.S. Application Data is a continuation-in-part of application No. 14/622,875, filed on Feb. 15, 2015, now Pat. No. 9,256,721, which is a continuation of application No. 14/265,811, filed on Apr. 30, 2014, now Pat. No. 8,959,361, which is a continuation of application No. 13/281,589, filed on Oct. 26, 2011, now Pat. No. 8,719,584.

(60) Provisional application No. 61/406,766, filed on Oct. 26, 2010.

(51) Int. Cl.
| | |
|---|---|
| *H04L 9/32* | (2006.01) |
| *G01N 33/497* | (2006.01) |
| *H04M 1/02* | (2006.01) |
| *G06F 1/16* | (2006.01) |
| *H04L 29/06* | (2006.01) |
| *H04W 12/06* | (2009.01) |
| *H04W 88/02* | (2009.01) |

(52) U.S. Cl.
CPC ............ *G06F 1/1684* (2013.01); *G06F 21/32* (2013.01); *G06K 9/00013* (2013.01); *G06K 9/00604* (2013.01); *H04L 63/0861* (2013.01); *H04M 1/0202* (2013.01); *H04W 12/06* (2013.01); *G06K 9/00885* (2013.01); *H04M 2250/12* (2013.01); *H04M 2250/14* (2013.01); *H04M 2250/22* (2013.01); *H04M 2250/52* (2013.01); *H04W 88/02* (2013.01)

(58) Field of Classification Search
USPC .................................... 726/2–7, 19; 713/186
See application file for complete search history.

(56) References Cited

U.S. PATENT DOCUMENTS

| | | | |
|---|---|---|---|
| 6,233,395 | B1 | 5/2001 | Bee |
| 6,289,113 | B1 | 9/2001 | McHugh et al. |
| 6,483,930 | B1 | 11/2002 | Musgrave et al. |
| 6,532,298 | B1 | 3/2003 | Cambier et al. |
| 6,917,902 | B2 | 7/2005 | Alexander |
| 6,950,536 | B2 | 9/2005 | Houvener |
| 7,016,532 | B2 | 3/2006 | Boncyk et al. |
| 7,346,195 | B2 | 3/2008 | Lauper et al. |
| 7,493,496 | B2 | 2/2009 | Smith et al. |
| 7,512,254 | B2 | 3/2009 | Volkommer et al. |
| 7,587,070 | B2 | 9/2009 | Myers et al. |
| 7,612,997 | B1 | 11/2009 | Diebel et al. |
| 7,689,005 | B2 | 3/2010 | Wang et al. |
| 8,381,573 | B2 | 2/2013 | Keays |
| 2003/0048175 | A1 | 3/2003 | Wang et al. |
| 2003/0093298 | A1 | 5/2003 | Hernandez et al. |
| 2005/0138394 | A1 | 6/2005 | Poinsenet et al. |
| 2005/0238208 | A1 | 10/2005 | Sim |
| 2005/0238210 | A1 | 10/2005 | Sim |
| 2006/0013446 | A1 | 1/2006 | Stephens |
| 2006/0013447 | A1 | 1/2006 | Siegel et al. |
| 2007/0297149 | A1 | 12/2007 | Richardson et al. |
| 2008/0212849 | A1 | 9/2008 | Gao |
| 2010/0183199 | A1 | 7/2010 | Smith et al. |
| 2011/0212699 | A1 | 9/2011 | Howard et al. |
| 2013/0219480 | A1* | 8/2013 | Bud ........................ G06F 21/32 726/7 |

OTHER PUBLICATIONS

Negin, Michael et al., "An Iris Biometric System for Public and Personal Use," IEEE Computer Society, Feb. 2001 pp. 70-75.

Xi, Kai et al., "Biometric Mobile Template Protection: A Composite Feature based Fingerprint Fuzzy Vault," IEEE International Conference on Communications, Jun. 2009.

Kang, Byung Jun et al., "A new multi-unit iris authentication based on quality assessment and score level fusion for mobile phones," Machine Vision and Applications vol. 21, Issue 4, Jun. 2010 pp. 541-553.

Motorola White Paper, "Mobile Biometric Identification," Motorola 2008 (Retrieved on Dec. 15, 2012) Retrieved from Internet: URL:http://www.motorola.com/web/Business/Products/Biometrics/Mobile%20AFIS/Mobile&20AFIS/_Documents/Static%20Files/Mobile20% Identifications%20White20%Paper.pdf—entire document.

Cox, "Eyeball-scanning iPhone used by cops to ID suspects," Networkworld.com, Jul. 21, 2011 (Retrieved on Dec. 27, 2012). Retrieved from the Internet: URL: http://www.networkworld.com/news/2011/072111-iphone-eyeball-scanning.html—entire document.

Biometric Technology Today, "Iris recognition for the masses?", ScienceDirect, vol. 14, Issue 6, Jun. 2006, p. 3-4, http://sciencedirect.com/science/article/pii/S0969476505410.

"Duratechinc, USA, Inc. Online Product Catalog retrieved via WebArchive", Published: Jul. 15, 2009, https://web.archive.org/web/20101101232018/http://www.duratechusa.com/Products?DA5-B.html.

"Amrel DA5-B review by RuggedPCReview.com", Published May 2009, http://ruggedpcreview.com/3_handhelds_amrel_da5b.html.

"Amrel: Mobile Biometric Solutins Slides", Published Jul. 14, 2009, http://www.wirelessmobiledata.com/amrel/mobilebiometric.pdg.

Product Description, "SPS 3000", Symbol, http://www.amerbar.com/catalog/sps3000.pdf, 2001.

* cited by examiner

MOBILE WIRELESS HAND-HELD IDENTIFICATION SYSTEM AND BREATHALYZER

RELATED APPLICATIONS

This application is a continuation-in-part of application Ser. No. 15/017,230, filed Feb. 5, 2016, which is a continuation-in-part of application Ser. No. 14/622,875, filed Feb. 15, 2015, now U.S. Pat. No. 9,256,721, which is a continuation of application Ser. No. 14/265,811, filed Apr. 30, 2014, now U.S. Pat. No. 8,959,361, which is a continuation of application Ser. No. 13/281,589, filed Oct. 26, 2011, now U.S. Pat. No. 8,719,584, which claims the benefit of provisional Application No. 61/406,766, filed Oct. 26, 2010, the entire contents of which is incorporated herein by reference.

FIELD OF THE INVENTION

The instant invention relates to biometric identification systems and more particularly to a mobile, hand-held biometric processing and communication systems which includes a data capture device for reading data from government issued identification credentials and further includes a breathalyzer module.

BACKGROUND OF THE INVENTION

Biometric identification systems based on fingerprints and the iris are well known in the prior art. For the most part, the prior art systems rely on fixed, i.e. wired, computer networks and they are not deployed in portable systems.

One biometric technology, that is a particular focus of the present invention, involves the visual examination of the attributes of the iris of the human eye. The iris of the human eye has random patterns of striations, ciliary processes, crypts, rings, furrows and other features which are shown to be capable of generating highly unique biometric templates for personal identification. Reference is made to U.S. Pat. No. 4,641,349, "Iris Recognition System", issued to Flom et al., and U.S. Pat. No. 5,291,560, "Biometric Personal Identification System Based on Iris Analysis", issued to Daugman. These patents are directed to biometric identification methods wherein the visible texture of a person's iris can be used to distinguish one person from another with great accuracy.

A typical iris recognition system, as currently known in the art, involves the use of an imager to video image the iris of a person to be identified, an encoding means for processing and encoding the image to produce a unique biometric template, and processing means for comparing the encoded template with templates stored in a database. Specific methods of generating templates and comparing templates are also well known in the art as exemplified by '560 patent to Daugman identified hereinabove. These templates may be used to identify individual irises in a 1-to-n comparison with extremely low error rates.

While these systems have been implemented in fixed installations with a high degree of success and market recognition, the prior art systems have been limited to fixed, hard-wired systems, which can leverage the speed and processing power of larger computer systems. The known iris identification systems capture the iris images using stationary optical platforms that are large, complex, and expensive, and the systems are difficult to use, even with cooperation of the subject being identified. As a result, their usefulness in many real-time applications is limited.

Although the art of biometric recognition systems is well developed, there still remain problems inherent in these technologies, particularly the lack of a portable or handheld device specifically designed to solve the problems inherent in capturing a close-up, high-quality, properly focused image of the face, or iris of the eye. Therefore, a need exists for a portable, hand-held biometric capture device that overcomes the drawbacks of the prior art.

SUMMARY OF THE INVENTION

The instant invention provides a biometric processing and communication system comprising a commercially available, handheld wireless communication device, such as an iPhone™, iPad™, Android™, or Blackberry™ mobile communication device, or other mobile communication device, and a dedicated biometric processing device piggybacked onto the communication device (iPhone™, iPad™, Android™, and Blackberry™ are trademarks of their respective owners). Associated software and processes enable the system, using commercially established wireless communication networks, to capture and process a digital image of a human biometric (fingerprint, iris, etc.) for transmission via a secure and encrypted internet connection to a central server. The device preferably includes at least one other data capture device which can read and capture at least one of a variety of other data types from a variety of different government issued credentials, such as passports, driver's licenses, green cards, visas and/or other identity cards. Even further, the device includes a breathalyzer module, which when used in conjunction with the biometric capture and data capture devices, can positively identify the person providing a breathalyzer sample.

The biometric processing device of the system is designed to focus on the difficult task of capturing the highest possible quality image for encoding and comparison. The process intensive tasks of encoding the obtained image to a digital template an then comparing the encoded template to all of the reference templates are not completed on the handheld system. Rather, the handheld system uses the established and functional technologies of the wireless communication device for transmitting the obtained image to a back-end server system. At the server level, the back-end server system receives the image, encodes the image of the biometric to a unique digital template, and compares the template with templates stored in a database to verify the identity of an individual previously enrolled in the database. If a match is obtained, the server transmits the identification data back to the handheld system for display on the system.

As indicated in the background, the core technologies for encoding biometric attributes to a unique template, and comparing the templates to render a match are known in the prior art. The back end server systems and database architecture for storing data are also well known in the art. Individuals are enrolled into the system by creating a database record including the individual's personal data, such as name, address, date of birth, social security number and a photograph. Each record also includes a biometric template, such as a fingerprint template, and/or an iris template obtained from the individual at the time of enrollment. In this manner, each individual enrolled in the system has a reference template for comparison.

Generally, the biometric processing and communication system comprises a commercially available handheld wireless communication device, such as an iPhone™, iPad™, Android™ cell phone or any other mobile PDA communication device, and a biometric processing device which is designed to work in conjunction with the wireless communication device. The system relies on the existing cell communication network to provide secure, reliable data communication between the system and the back-end database server of the system. The system also utilizes the existing touch screen display of the wireless communication device for input/output of the system, display of a graphical user interface system, and display of images from the capture module during the image acquisition process.

The handheld wireless communication device comprises a housing having an external surface, a central processing unit, a battery power source, a touch screen display, a long range wireless communication transceiver (cell, wi-fi or RF), a short range wireless communication transceiver (Bluetooth or Ultra-Wide Broadband (UWB) and an electrical input/output (I/O) connector.

The biometric processing device comprises a housing having an interior cavity contoured to conform to the exterior surface of the housing of the handheld wireless communication device, a docking port including an electrical input/output (I/O) connector within the interior cavity, and a window in a front surface thereof in communication with the interior cavity.

The handheld wireless communication device is removably seated in mated relation within the interior cavity of the housing of the biometric processing device wherein the touch screen display of the handheld communication device is accessible through the window of the housing of the biometric processing device.

The biometric processing device further comprises a biometric capture module, a short range wireless communication transceiver, a central processing unit, and a battery power source. A software application running on the central processing unit of the biometric processing device is operative for sending data to and receiving data from the wireless communication device through either the short range wireless communication transceivers or the electrical I/O connectors, controlling the biometric capture module to capture an image of a biometric attribute of a person to be identified, qualifying the captured image as being of acceptable quality for encoding into a biometric template, and transferring the qualified image to the wireless communication device.

Another software application runs on the central processing unit of the handheld wireless communication device and is operative for providing a graphical user interface on the touch screen display for control of the biometric processing device and the wireless communication device. The software application receives control input from a user through the touch screen display, communicates the control input to the central processing unit of the biometric processing device through the short range wireless communication transceiver or the electrical I/O connectors, receives the qualified image from the biometric processing device, communicates with a communication network through the long range wireless communication transceiver, communicates with a remote computer network connected to the communication network, transmits the qualified image over the communication network to the computer network for encoding the qualified image to a biometric attribute template and comparison of the encoded biometric attribute template to a plurality of reference templates stored in the network accessible database, receives identification data from the computer network over the communication network responsive to the comparison, and displays the identification data on the touch screen display.

Of particular concern and interest for the present invention is the acquisition of the highest possible quality image for transmission back to the server. One of the fundamental problems in implementing a mobile system is the acquisition of a quality image for encoding and comparison. The prior art systems rely on highly complex, fixed systems which can reliably acquire a high-quality image.

The present system provides a unique division of processing where the biometric processing device focuses on obtaining a high-quality image, and the back end server is used to encode the image and compare the image. The division of processing power provides the ability to quickly obtain the iris image at the point of identification, and then once the image is transmitted, the high-power servers can quickly process the image, encode the image and compare it to the database for verification of identification. Once the image is transmitted to the server, the server can encode, compare and provide results in under 5 seconds. This unique division of resources and computing power allows the biometric processing system to only focus on the critical job of obtaining a high-quality image for encoding.

Once the results are provided, the end user can have access to a variety of different information linked to the identified individual. The system can be linked to criminal records database to return outstanding warrants, or to a health care system to return critical health information for a health care provider.

Additionally, the data capture device permits the end user to scan a presented identification credential and cross check the data against another database. This can verify identify, verify forged credentials and/or confirm the use of a stolen credential. The data capture device can comprise any one of a barcode scanner, smart card reader, magnetic stripe reader, machine readable zone (MRZ) reader, HID reader, RFID reader, signature capture, etc.

As a further tool for law enforcement, the breathalyzer module will allow law enforcement to capture a breathalyzer sample and concurrently capture identification credentials and other biometric data to positively link the breathalyzer sample with the person providing the sample.

Accordingly, among the objects of the instant invention are: the provision of a hand-held biometric processing device that cooperates with a commercially available wireless communication device to capture, process and store a digital image of a human biometric attribute;

the provision of a hand-held biometric processing device that uses the communication services of the wireless communication device to communicate with a remote server using commercially available wireless networks;

the provision of a hand-held biometric processing device that enables a user to capture a high-quality digital image of a human biometric attribute;

the provision of a hand-held biometric processing device that also includes a fingerprint acquisition module;

the provision of a hand-held biometric processing device that also includes a data capture module;

the provision of a hand-held biometric processing device that also includes a breathalyzer module;

the provision of a hand-held biometric processing device that utilizes the existing display and input/output interfaces (wired and/or wireless) of a commercially available wireless communication device to operate the biometric/data capture/breathalyzer processing device.

Other objects, features and advantages of the invention shall become apparent as the description thereof proceeds when considered in connection with the accompanying illustrative drawings.

DESCRIPTION OF THE DRAWINGS

In the drawings which illustrate the best mode presently contemplated for carrying out the present invention.

DESCRIPTION OF THE PREFERRED EMBODIMENT

Figure 1:
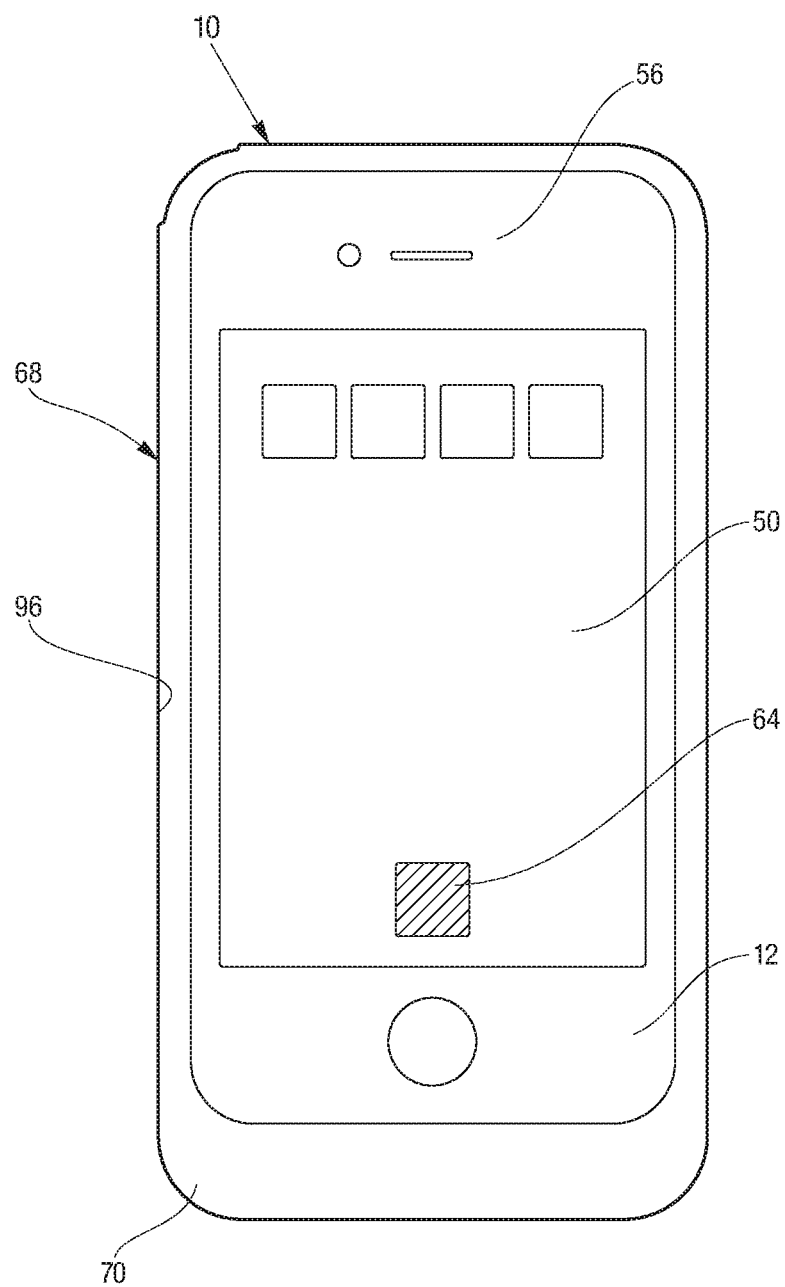
FIG. 1 is a front view of the processing and communication system in accordance with the teachings of the present invention.

Referring now to the drawings, the biometric and data processing and communication system of the instant invention is illustrated and generally indicated at 10 in FIGS. 1-11. As will hereinafter be more fully described, the instant invention provides a biometric and data processing and communication system 10 comprising a commercially available wireless communication device generally indicated at 12, a biometric processing device generally indicated at 14, and associated software and processes which enable the handheld wireless communication device 12, using commercially established wireless communication networks, to capture and process a digital image 16 of a human biometric attribute, for transmission via a secure and encrypted internet connection to a remote server and to capture readable data for transmission to a remote server.

The term "human biometric attribute" or "biometric attribute" is intended to encompass fingerprints, facial features, iris, retina, and any other attribute, which is unique to an individual and can be scanned and compared to a reference. The present disclosure focuses primarily on the human iris and secondarily fingerprints. However, the scope of the invention should not be so limited to any attribute listed herein. The focus of the invention is the provision of a portable hand-held system that captures a high-quality image 16 and then uses the existing communication links of an established communication system to transmit the captured image 16 to a remote server for encoding into a digital template and comparison to a plurality of reference templates stored in a database.

The term "readable data" is intended to encompass any type of data that can be read from an identification document (not shown). Currently, data is printed, encoded or stored by various means on government or agency issued identification documents, such as passports, driver's licenses, green cards, visas and/or other identification cards. Various technologies are available for reading this data, including but not limited to barcode scanners, smart card readers, magnetic stripe readers, machine readable zone (MRZ) readers, HID readers, RFID readers and signature capture devices. These are generally referred to as data capture devices or data capture modules.

The term "breath sample" is intended to encompass breath content data as acquired by a conventional breathalyzer device. Breathalyzer devices are well known in the art and generally are capable of taking a breath sample from an individual and identifying the alcohol content and in turn the blood alcohol level of the individual. An example of such as breathalyzer device or module is illustrated and described in U.S. Pat. No. 8,381,573, the entire contents of which are incorporated herein by reference.

Figure 9:
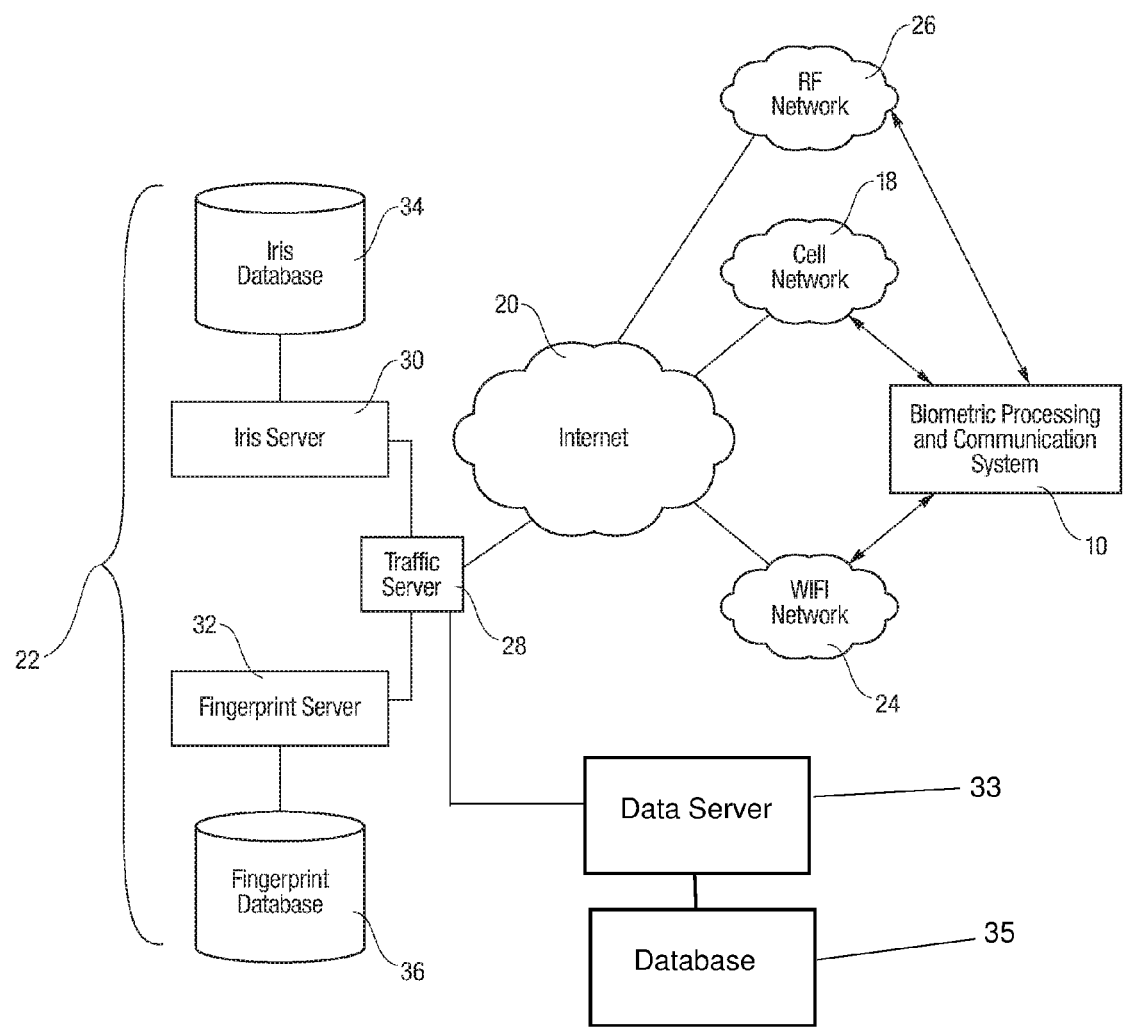
FIG. 9 is a schematic block diagram of the overall communication network between the wireless communication device and the back end database server.

A block diagram of the overall system is best illustrated in FIG. 9. At the handheld system level, the biometric and data processing and communication system 10 captures an image 16 of a biometric attribute of the individual to be identified. The handheld system 10 transmits that image or a template of that image through an existing cell communication network 18, through the world-wide web 20 and eventually to a remote server system 22. Alternatively, the image 16 could be transmitted through a secure WIFI network 24 provided at the local site level, or even further through an existing radio (RF) network 26. On the data capture side, the system 10 captures data from an identification document presented by the individual in question. The device 10 also transmits that data over the existing communication networks. The system 10 can further capture a breath sample of the individual, and using the biometric data and identification document data, can positively link the breath sample to the individual it was captured from.

At the server system 22, a traffic server 28 receives the acquired image 16 or other data, directs the image 16 and/or other data to an appropriate encoding/comparison server 30, 32, 33 based on the type of image 16 (iris or fingerprint) or data. The server(s) 30 and 32 encode(s) the image 16 to a unique digital template, and compares the template with templates stored in a database 34, 36 to verify the identity of an individual previously enrolled in the database 34, 36. The results of the comparison are then in turn transmitted back to the handheld system 10 to provide identification, verify identification or indicate there is no match. In the case of captured data, the server 33 compares the captured data with personal data stored in the connected database 35. The data server 33 and database 35 could be part of any issuing agency network system.

In the context of the present invention, it is currently preferred that separate databases 34, 36 will be maintained for identifying individuals based on iris templates or fingerprint templates. The reason for separating the databases 34, 36 is primarily to improve encoding and matching speeds. However, it should be noted that there are limitless possibilities for the architecture of the back-end server systems and databases, and that the illustrated embodiment is just one demonstrative example.

Once identification is verified, the servers 28, 30, 32 may also be connected to other databases (not shown), such as a criminal records database or a health care database, and can return further information to the end user. In this regard, the data capture capabilities permit the end user to alternatively verify identity using presented identification credentials (if the individual is not in the iris or fingerprint databases), to detect forged identification documents, or to identify stolen or borrowed credentials. Potential ends users include, but are not limited to, police officers and sheriffs in the field, border patrol agents in the field, field nurses, doctors, and EMT's at the scene of an accident.

In law enforcement, field sobriety tests and breathalyzer tests are important tools for policing drunk drivers. Breathalyzer test results are critical in the process of enforcement and are routinely used during trials as evidence. However, defense counsel often question the evidence based on procedure, chain of title, and proper identification of the individual providing the sample. The integration of a breathalyzer device in the present system removes a key challenge to the use of such evidence by biometrically linking the breath sample directly to the individual providing the sample. Outside of law enforcement, breathalyzer results are used in other situations and the present device would also be useful in those instances as well to link the sample to the individual providing the sample.

As indicated in the background, the core technologies for encoding the images 16 of the biometrics to unique digital templates, and comparing the templates to those in an existing database to render a match are known in the prior art.

In accordance with the invention, individuals are enrolled into the system by creating a database record including the individual's personal data, such as name, address, date of birth, and social security number. Each record also includes a facial photograph and/or an iris image and template, and/or a fingerprint image and template, each obtained from the individual at the time of enrollment. In this manner, each individual enrolled in the system has a unique reference template for comparison.

Turning back to FIGS. 1-8, the biometric processing and communication system 10 comprises a processing device 14 which is intended to work in conjunction with a commercially available wireless communication device 12 such as an iPhone™, iPad™, Android™, or Blackberry™ cell phone, or any other mobile PDA communication device. While these specific devices are identified herein, the scope of the invention is not intended to be limited to either of these devices. Any mobile wireless device could serve as the communication part of the proposed capture and processing system.

Figure 6:
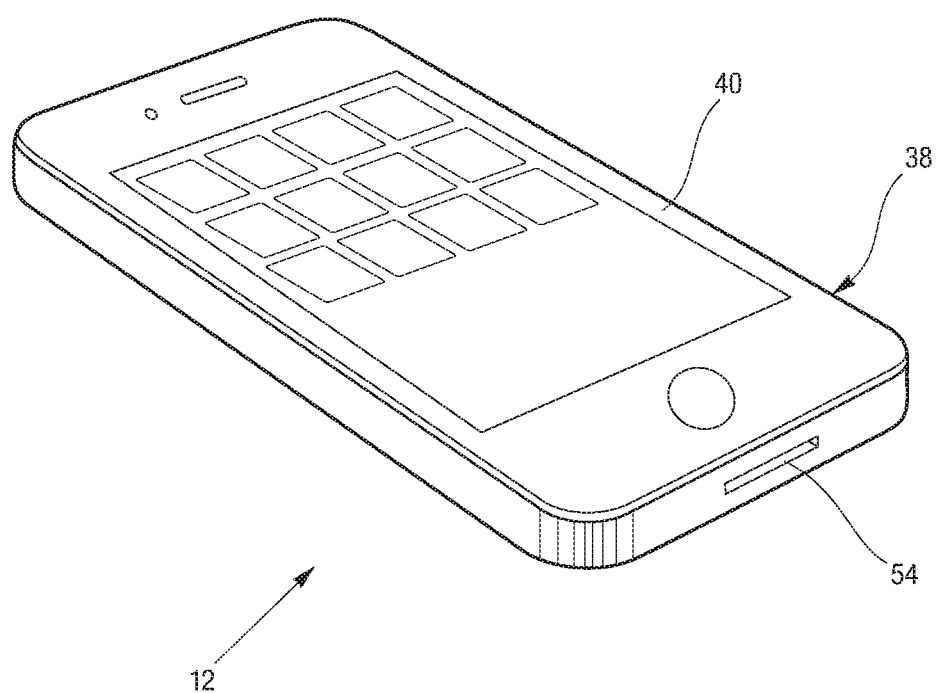
FIG. 6 is a perspective view of a representative wireless communication device.
Figure 7:
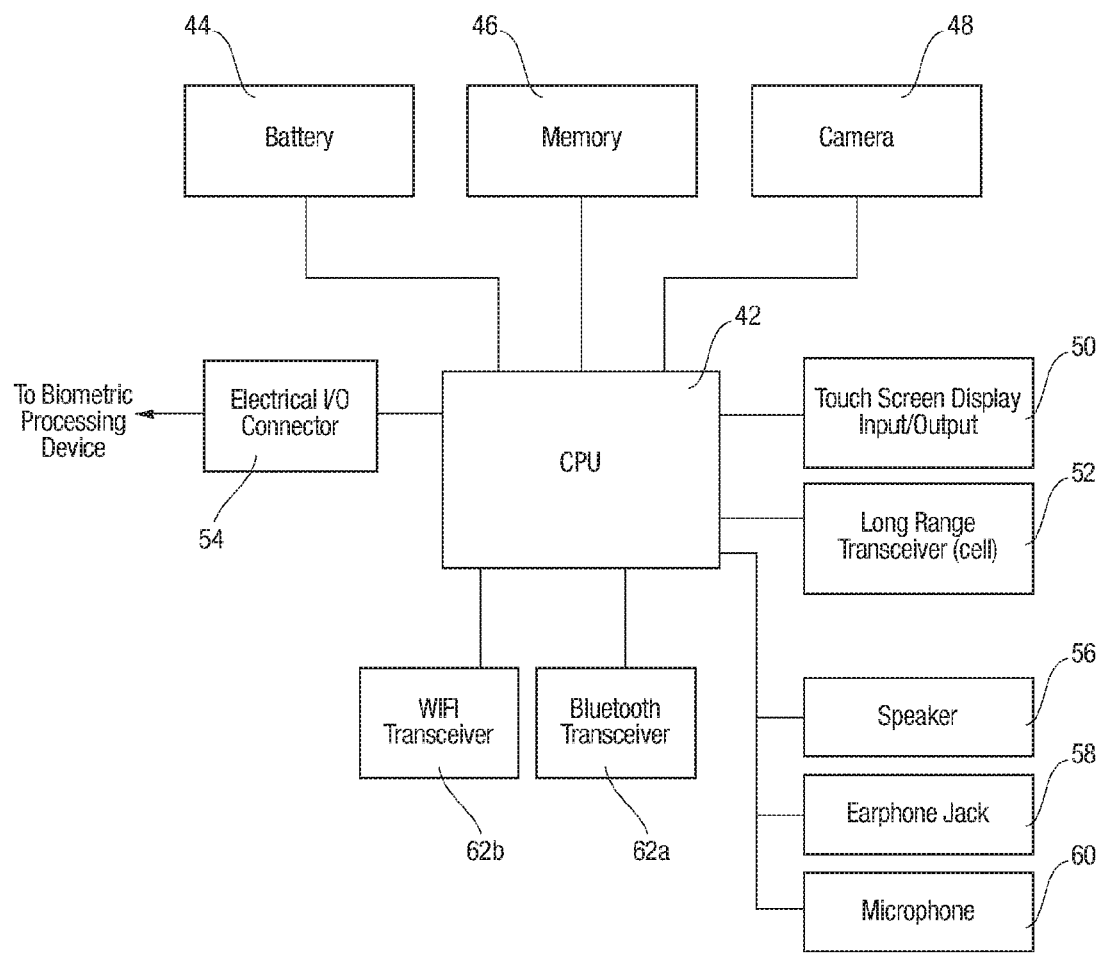
FIG. 7 is a schematic block diagram of the electronic components of the wireless communication apparatus.
Figure 8:
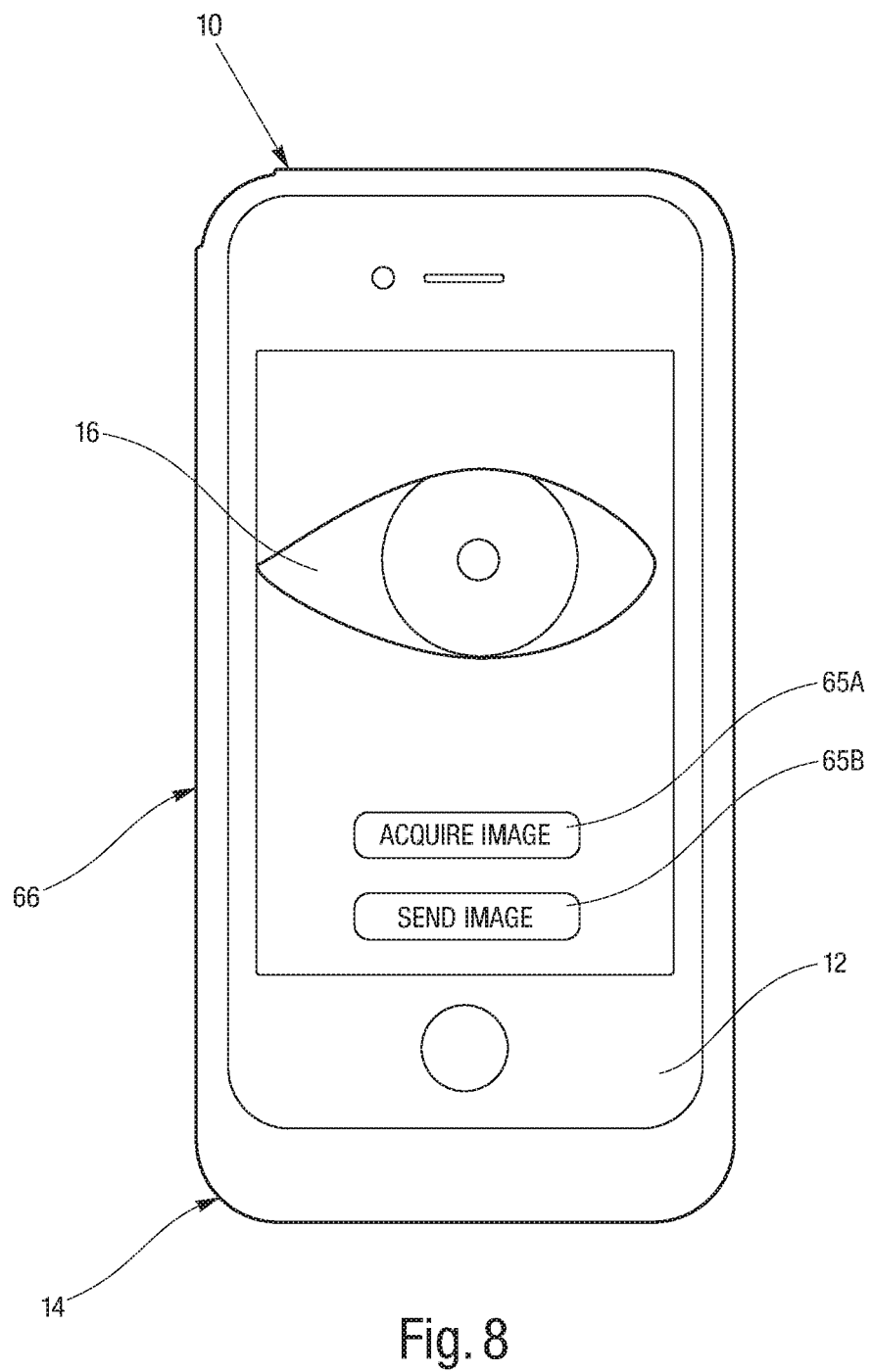
FIG. 8 is a front view of the processing and communication system showing the graphical user interface displayed on the wireless communication device.

For purposes of description only, an iPhone™ device is illustrated in FIGS. 6 and 7 as a representative handheld wireless communication device 12. However, the scope of the invention should not be limited by the specific details of this one device. More specifically, referring to FIGS. 6 and 7, the handheld wireless communication device 12 generally comprises a housing 38 having an external surface 40, a central processing unit (CPU) 42, a battery power source 44, a memory 46, a digital camera 48, a touch screen display 50, a long range communication transceiver 52, and an electrical input/output (I/O) connector 54 for communicating with external devices such as the biometric processing device 14, and/or a computer, battery charger, etc. The handheld wireless device 12 further includes a speaker 56, earphone jack 58, and a microphone 60. Still further, the device 12 includes a short-range communication transceiver 62, such as a Bluetooth transceiver 62A and/or a WIFI transceiver 62B. The architecture and functioning of these components are all well-known in the art.

The processing device 14 relies on the existing cell communication network 18 as used by the wireless communication device 12 (iPhone™) to provide secure, reliable data communication between the handheld system 10 and the back-end database server 22 of the system. The biometric processing device 14 also utilizes the existing touch screen display 50 of the wireless communication device 12 (iPhone™) for input/output of the device 14, display of a graphical user interface system, and display of images 16 from the biometric processing device 14 during the image acquisition process.

A proprietary software application is loaded onto the wireless communication device 12 (see FIG. 1—MORIS™ icon 64) to provide an easy to use graphical user interface (GUI) and controls for establishing communication with the back-end server 22, acquiring the images 16 and then sending the images 16 to the server 22 for encoding and matching with the databases 34, 36 (MORIS™ is a trademark of BI2™ Technologies, LLC). The GUI is also used for controlling acquisition of each biometric image 16, i.e. iris or fingerprint, or data set.

As indicated above, of particular concern and interest for the present invention is the acquisition of the highest possible quality image 16 of the iris for transmission back to the server 22. One of the fundamental problems in implementing a mobile biometric iris identification system is the acquisition of a quality image 16 for encoding and comparison. The prior art systems rely on highly complex, fixed systems with expensive lenses and video capture devices which can reliably acquire a high-quality image.

Referring again to FIGS. 1-5, the capture and processing device 14 comprises a compact housing 66 including a rear portion 68 and a front portion 70 which snap together to form a ruggedized shell for enclosing the wireless communication device 12. The rear housing portion 68, best illustrated in FIG. 4 houses the various components of the capture device 14. The front surfaces 72 of the rear housing portion 68 and the rear surfaces (not shown) of the front housing portion 70 are contoured to conform to the exterior surface 40 of the wireless communication device 12 so that it is snugly seated and secured within an interior cavity 74 (shown in broken line in FIG. 3) within the device 14. Different housing versions will be required for the various different mobile communication devices. The interior bottom wall includes an electrical input/output (I/O) connector 76, which mates with the connector 54 of the wireless communication device 12 to provide communication and data transfer between the two devices 12, 14. The connector 76 will obviously match the respective connector 54 of the wireless communication device 12. In the case of the iPhone™ as illustrated, the top corner of the rear housing portion 68 includes an aperture 78 for the existing camera 48 on the wireless communication device 12. The aperture 78 may be in a different location for a different device.

Figure 2:
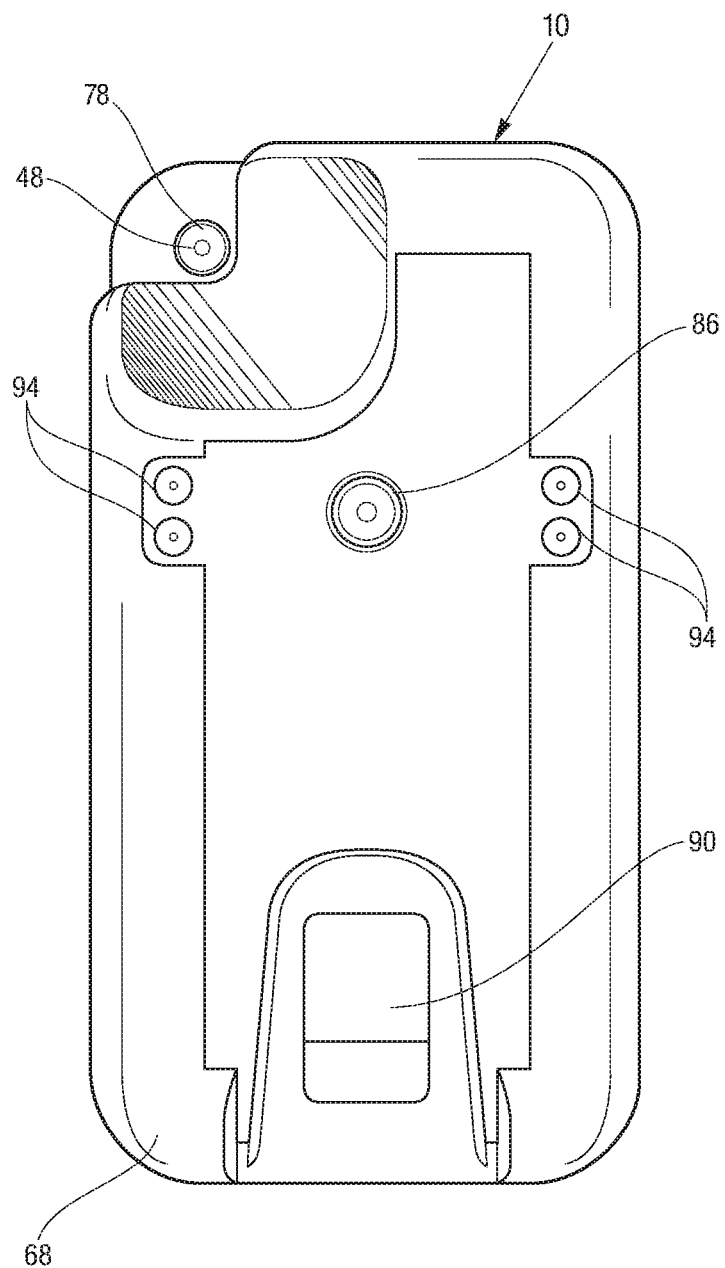
FIG. 2 is a rear view thereof.
Figure 3:
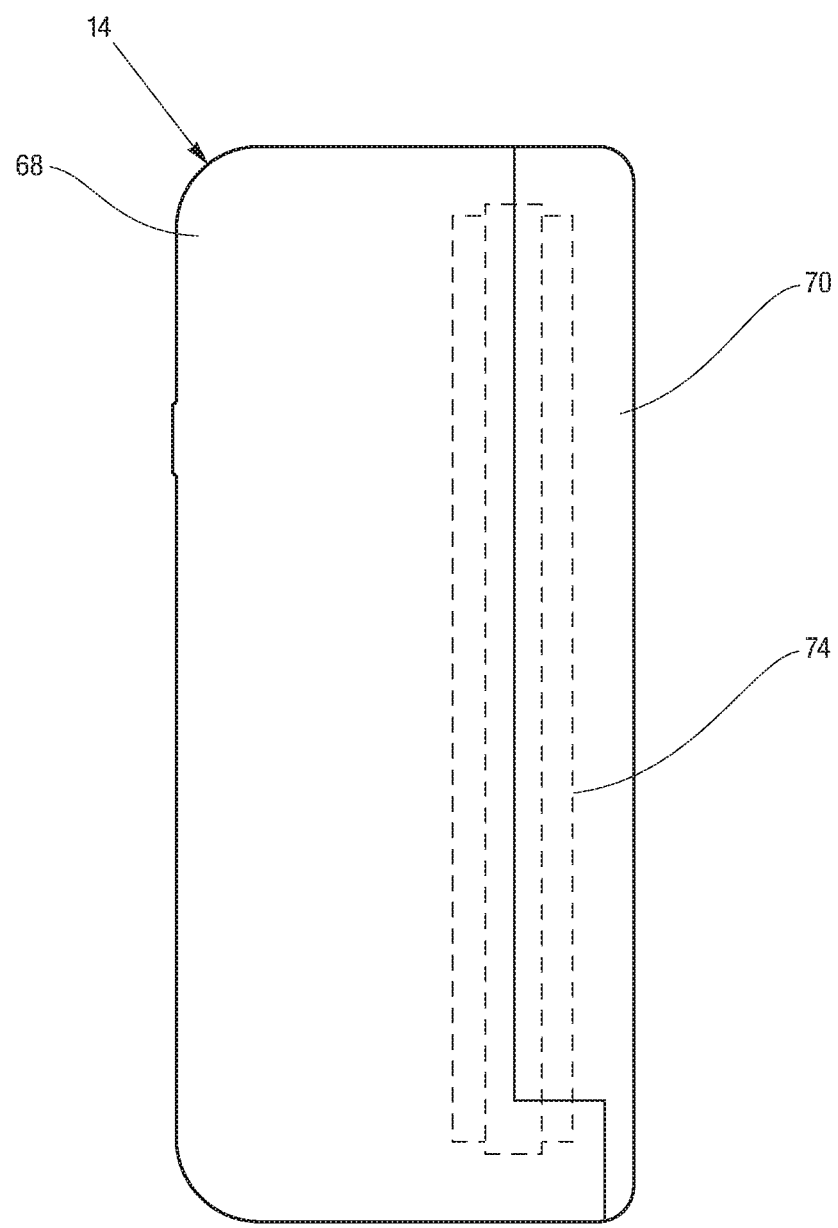
FIG. 3 is a side view thereof.
Figure 4:
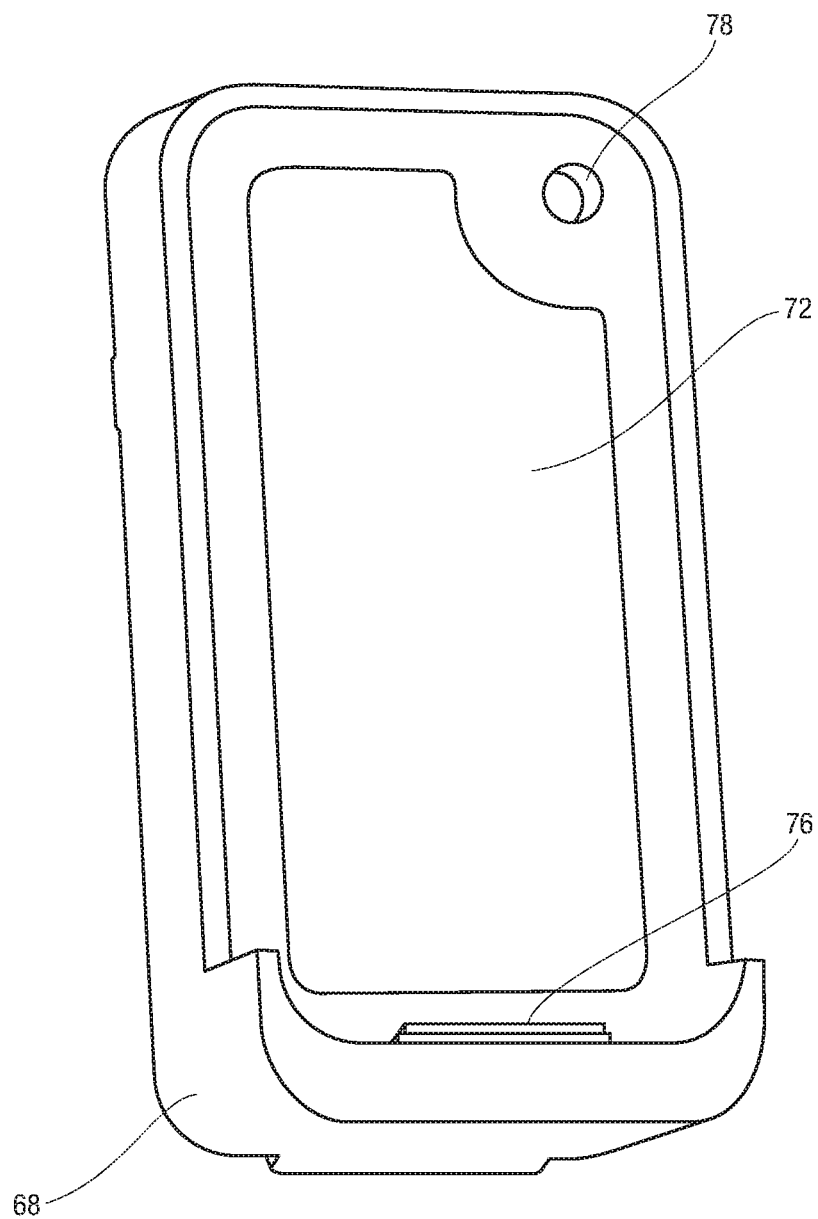
FIG. 4 is a perspective view of the rear housing portion of the processing device showing the internal connector for wired communication with the wireless communication apparatus.
Figure 5:
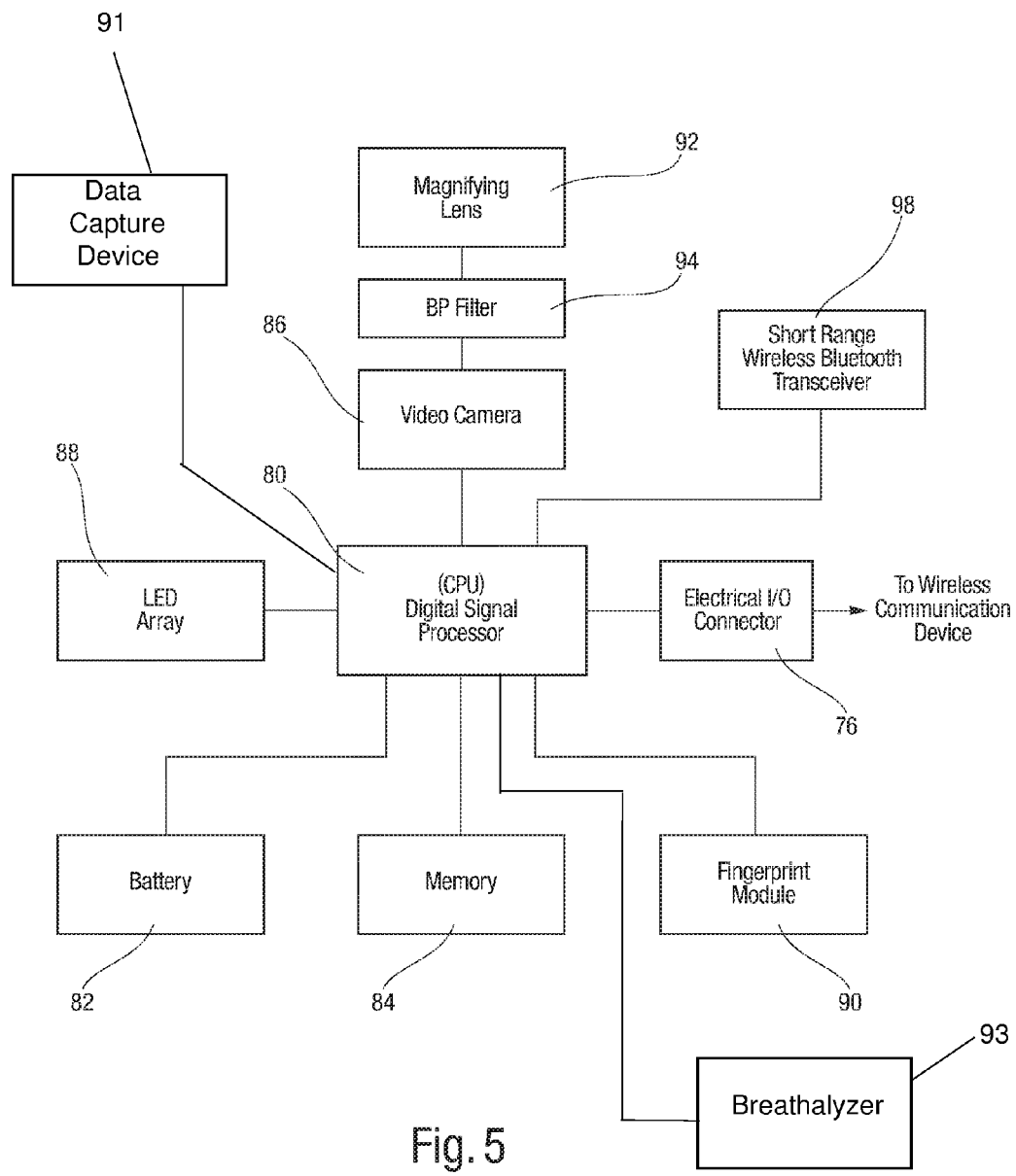
FIG. 5 is a schematic block diagram of the electronic components of the processing device.

Referring to FIGS. 2 and 5, the processing device 14 comprises a central processing unit (CPU) 80, which is preferably a high power Digital Signal Processor (DSP) selected for high-speed processing of digital video images, a battery power supply 82, memory 84, a high quality digital camera 86 selected specifically for high quality video imaging of the iris, an LED array 88 for illuminating the iris, and a fingerprint capture module 90 for alternate or redundant biometric identification.

The device 14 further comprises one or more data capture devices 91 which can be selected from one of many known data capture technologies, including barcode scanners, smart card readers, magnetic stripe readers, machine readable zone (MRZ) readers, HID readers, RFID readers and signature capture devices.

A breathalyzer module is generally indicated at 93. As noted above, the specific details of such devices are known in the art, and a representative example is identified and incorporated herein above in the '573 patent. It is contemplated that the breathalyzer components 93 can be incorporated directly into the housing 66 where it would communicate by wired connection (FIG. 5) or the entire breathalyzer device 93 could be provided separately and communicate with the device 14 or the phone 12 wirelessly through one of the provided wireless transceivers. Breath sample data may be retained locally on the device in memory 84 and/or may be transmitted to the backend server system for storage and later use.

The iris camera 86 is provided with a magnifying lens 92 selected for close up imaging of the iris as well as a 780 nm band pass filter 94 for blocking unwanted light wavelengths. The LED array 88 includes infra-red LED's 94 which illuminate and enhance the structural features of the iris for image acquisition. The use of near IR illumination and band-pass filters for iris imaging is known in the art.

The front housing portion 70 includes a large window 96 to provide access to the touch screen display 50 of the wireless communication device 12 mounted therein.

Before turning to a description of the processes for acquiring and transmitting the images of the biometric attributes, we pause to briefly discuss communication between the handheld communication device 12 (iPhone or otherwise) and the biometric processing device 14. There are two primary means of communication between the two devices. There is a direct wired connection between the I/O connector 54 of the wireless communication device 12 and the I/O connector 76 of the biometric processing device 14. This is the preferred path of communication since it provides a direct wired connection. This path is bi-directional wherein control input from the wireless communication device 12 is passed from the wireless communication device 12 to the biometric processing device 14 for control thereof.

However, with respect to the illustrated embodiment, Apple™, by design, throttles the speed of any image data being transferred to the iPhone 12, which controls any outside use of image and video data not acquired through the proprietary iTunes™ interface (Apple™ and iTunes™ are trademarks of Apple, Inc.). This restriction seriously impedes the speed at which the acquired biometric image 16 can be transferred from the biometric processing device 14 to an iPhone 12 for subsequent transfer to the back-end servers 22. Accordingly, in iPhone device platforms, the biometric processing device 14 further includes a short range wireless transceiver 98, for example, a Bluetooth transceiver, which wirelessly communicates with a like transceiver 62 (Bluetooth) in the wireless communication device 12 to transfers data between the devices 12, 14. In this regard, all data in both directions is communicated through this wireless connection. Other short range transceivers are also contemplated, such as Ultra-Wide Broadband (UWB) transceivers. The standard wired I/O ports can be used with other cellular phone platforms.

Figure 10:
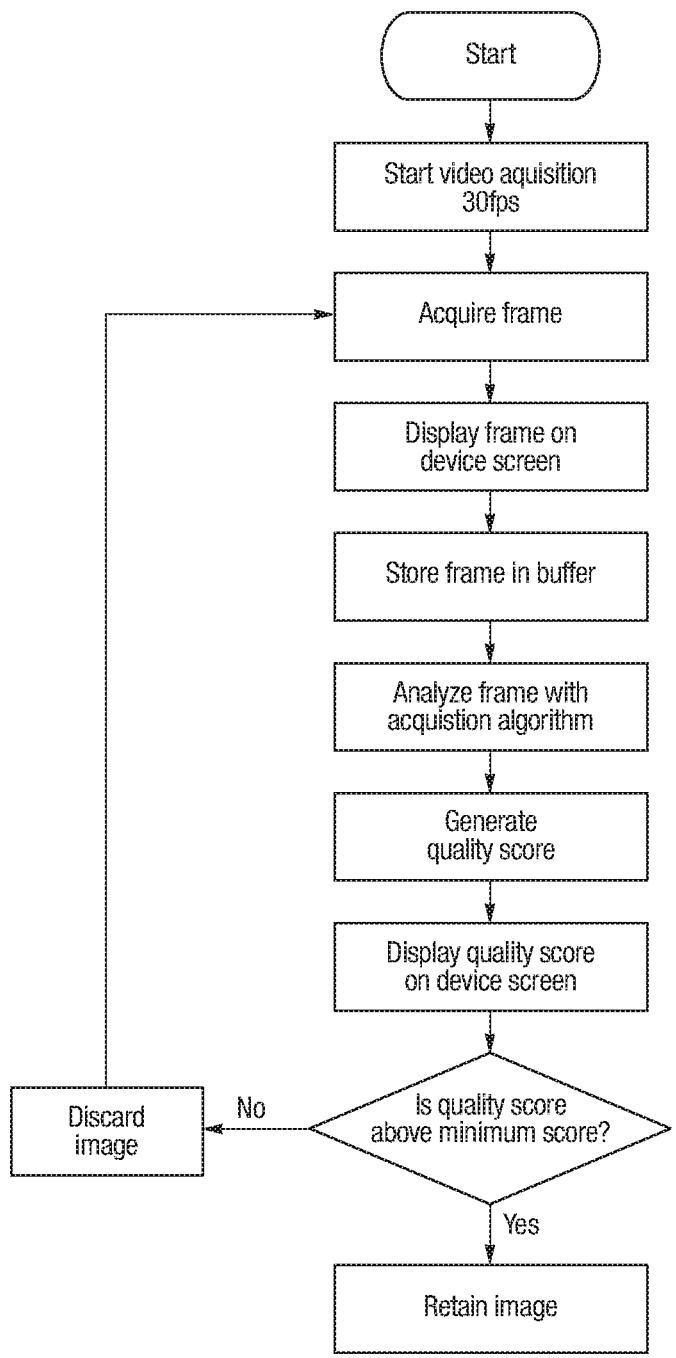
FIG. 10 is flow diagram illustrating the process for acquiring an iris image using the biometric processing device.
Figure 11:
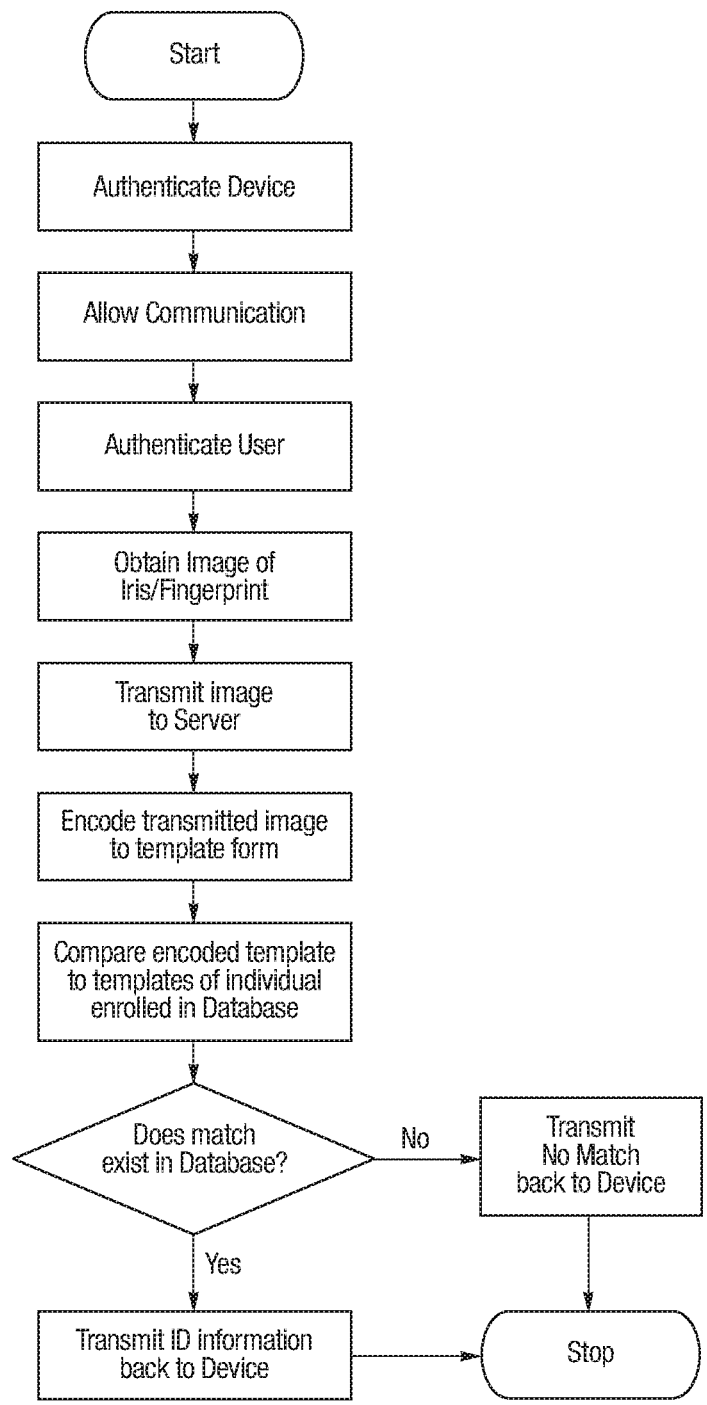
FIG. 11 is a flow diagram illustrating the overall process for acquiring the biometric attribute, transmitting the biometric attribute and verifying the identity of the individual from which the biometric attribute was acquired.

Turning to FIG. 10, there is shown a representative flow chart illustrating the steps for acquiring an iris image. While acquisition of the iris image is the focus of FIG. 10, the flow chart represents the general process parameters for the acquisition of a fingerprint image as well.

As described hereinabove, the present system provides a unique division of processing where the hand-held capture device 14 focuses on obtaining a high-quality image 16 of the biometric attribute, and the back end servers 22 are used to encode the image and compare the image. The division of processing power provides the ability to quickly obtain the biometric image 16 at the point of identification, and then once the image 16 is transmitted, the high-power servers 22, 30, 32 quickly process the image 16, encode the image 16 and compare it to the database(s) 34, 36 for identification or verification of identification. Once the image 16 is transmitted to the servers, the servers can encode, compare and provide results in under 5 seconds. This unique division of resources and computing power allows the biometric capture device 14 to only focus on the critical job of obtaining a high-quality image for encoding.

Turning back to FIG. 10, there is a flow chart showing the basic process for acquiring the iris image. In this regard, the DSP runs its own internal software application to control acquisition of the biometric images. The iris image acquisition process uses a continuous stream of video images of the iris to obtain a high number of images for analysis and selection. Briefly, the DSP 80 selected for the biometric processing device is uniquely suited for high-speed video processing. Once the acquisition process is initiated, the DSP 80 receives a video stream from the iris camera 86 at a rate of 30 frames per second. Note, that other frame rates may also be used depending on the camera device 86, DSP 80 and biometric attribute. Once the acquisition stream is started, each frame is buffered, and analyzed for focus and quality. Each image 16 is given a quality score (qualified) based on an algorithm in the analyzing software. A critical aspects of the invention is that the DSP 80 is effective for analyzing each frame in real-time. As soon as one image 16 is acquired which meets a minimum quality score (qualified) it is temporarily stored into a memory location 84 and then transferred to the wireless communication device 12 through either the short range wireless connection (short range transceivers 62, 98) iPhone™ or a wired I/O connections 54, 76 (Android™ or other communication devices).

In an alternative, the biometric processing device 14 could analyze all of the frames as the video stream continues, and if another image receives a higher quality score, the stored image is discarded and the higher score image is stored in its place. Alternatively, multiple images might be stored. After a fixed period of time, for example 10 seconds of running video, the acquisition process terminates.

The fingerprint acquisition process is generally the same, except it is not based on a stream of video frames. Rather the user places a finger onto the fingerprint pad and the DSP initiates a routine which scans the fingerprint to obtain an appropriate fingerprint image according to the specifications of the fingerprint module. The operation of such fingerprint modules 90 is well-known in the art.

If at least one image 16 meeting the minimum quality score is acquired, the image 16 is then be transmitted to the servers 22, 30, 32 through the communication link, encoded at the servers, and compared to the database(s). Results of the comparison are then transmitted back to the device 10 along with additional information corresponding to the end user needs.

As a secondary identification check, the end user can scan, swipe or otherwise capture data from a presented identification credential such as a passport or driver's license, etc. The device 10 is operable for receiving data capture control input through the touch screen 50, communicates the control input to the central processing unit of the device 10, receives the captured data, and then controls communication with the computer network through the wireless transceiver. The captured data is compared at server 33 and identification data is returned and displayed on the screen 50.

A plurality of data capture devices 91 can be integrated into a single device 10 to provide universal capabilities in all situations and across all types of credentials.

As indicated above, police officers, sheriffs or border patrol agents may receive information relating to prior arrests or outstanding warrants, military personnel in the field may receive priority security alerts once a person is identified, or a nurse, doctor or EMT in the field could receive critical health care information for an injured person. The system 10 could also find everyday use in the healthcare industry to confirm the identity of sedated individuals prior to surgery or prior to dispensing of medicines. Law enforcement agencies can use the system 10 to verify the identity of offenders being booked into the criminal justice system or being released from the criminal justice system. Incidences of identify fraud in prison releases is a growing concern.

While there is shown and described herein certain specific structure embodying the invention, it will be manifest to those skilled in the art that various modifications and rearrangements of the parts may be made without departing from the spirit and scope of the underlying inventive concept and that the same is not limited to the particular forms herein shown and describe.

What is claimed is:

1. An identification system comprising:
    a handheld wireless communication device comprising
        a housing,
        a central processing unit,
        a touch screen display,
        a wireless communication transceiver and
        an input/output (I/O) connector;
    a processing device comprising
        a housing having
            an interior cavity configured to receive said housing of said handheld wireless communication device,
            a docking port including an input/output (I/O) connector within said interior cavity, said handheld wireless communication device being seated within said interior cavity of said housing
            wherein said I/O connector of said handheld wireless communication device is mated with said I/O connector of said processing device,
            and further wherein said touch screen display of said handheld communication device is accessible through a window of said housing of said processing device,
    said processing device further comprising
        a biometric capture module,
        a data capture module,
        a breathalyzer module,
        a central processing unit, and
        a first software application running on said central processing unit of said processing device operative for
            sending data to and receiving data from said wireless communication device through said mated I/O connectors,
            controlling said biometric capture module to capture an image of a biometric attribute of a person to be identified, and
            controlling said data capture module to capture data from an identification document,
            controlling said breathalyzer module to capture a breath sample; and
        a second software application running on said central processing unit of said handheld wireless communication device operative for providing a graphical user interface on said touch screen display for control of said processing device and said wireless communication device, said second software application
            receiving biometric capture control input, data capture control input and breathalyzer control input,
            communicating said control inputs to said central processing unit of said processing device through said mated I/O connectors,
            receiving output data from said processing device,
            controlling communication with a communication network through said wireless communication transceiver,
            controlling communication with a remote computer network connected to said communication network,
            transmitting said output data over said communication network to said computer network for identification,
            receiving identification data from said computer network over said communication network, and
            displaying said identification data on said touch screen display.

2. The identification system of claim 1 further comprising a second biometric capture module for capturing a second biometric attribute of said individual to be identified, said second biometric attribute comprising a fingerprint, said second biometric capture module comprising a fingerprint capture module.

3. The identification system of claim 1, wherein said wireless communication device includes a digital camera having a lens, said housing of said processing device having a camera window in communication with said interior cavity, said lens being located within said camera window of said housing when said wireless communication device is seated within said interior cavity.

4. The identification system of claim 1, wherein said data capture module is selected from the group consisting of: barcode scanner, smart card reader, magnetic stripe reader, machine reader zone (MRZ) reader, HID reader, RFID reader, and signature capture device.

5. An identification system comprising:
    a wireless communication network;
    a computer network in communication with said communications network;
    a first network accessible database storing a plurality of database records, each database record including biometric data associated with an individual;
    a second network accessible database storing a plurality of database records, each database record including personal data associated with an individual;
    a first computer server in communication with said computer network,
    first server software on said first computer server for comparing obtained biometric data to stored biometric data;
    a second computer server in communication with said computer network;
    second server software on said second computer server for comparing captured data to stored personal data;
    a handheld wireless communication device comprising
        a housing,
        a central processing unit,
        a touch screen display,
        a wireless communication transceiver and
        an input/output (I/O) connector;
    a processing device comprising
        a housing having
            an interior cavity configured to receive said housing of said handheld wireless communication device
            a docking port including an input/output (I/O) connector within said interior cavity, said handheld wireless communication device being seated within said interior cavity of said housing
wherein electrical I/O connector of said handheld communication device is mated with said I/O connector of said processing device,
and further wherein said touch screen display of said handheld communication device is accessible through said window of said housing of said processing device,
said processing device further comprising
a biometric capture module,
a data capture module,
a breathalyzer module,
a central processing unit,
a first software application running on said central processing unit of said processing device operative for
sending data to and receiving data from said wireless communication device through said mated I/O connectors,
controlling said biometric capture module to capture an image of a biometric attribute of a person to be identified,
controlling said data capture module to capture data from an identification document,
controlling said breathalyzer module to capture a breath sample; and
a second software application running on said central processing unit of said handheld wireless communication device operative for providing a graphical user interface on said touch screen display for control of said processing device and said wireless communication device, said software application
receiving biometric capture control input, data capture control input and breathalyzer control input,
communicating said control inputs to said central processing unit of said processing device through said mated I/O connectors,
receiving output data from said processing device,
controlling communication with said communication network through said wireless communication transceiver,
controlling communication with said computer network connected to said communication network,
transmitting said output over said communication network to said first computer server for identification,
receiving identification data from said first computer server through said computer network and said communication network responsive to said comparison, and
displaying said identification data on said touch screen display.

6. The identification system of claim 5 further comprising a second biometric capture module for capturing a second biometric attribute of said individual to be identified, said second biometric attribute comprising a fingerprint, said second biometric capture module comprising a fingerprint capture module.

7. The identification system of claim 5, wherein said wireless communication device includes a digital camera having a lens, said housing of said processing device having a camera window in communication with said interior cavity, said lens being located within said camera window of said housing when said wireless communication device is seated within said interior cavity.

8. The identification system of claim 5, wherein said data capture module is selected from the group consisting of: barcode scanner, smart card reader, magnetic stripe reader, machine reader zone (MRZ) reader, HID reader, RFID reader, and signature capture device.

9. A method of identifying a person based on a biometric identifier and captured data comprising the steps of:
providing a handheld wireless communication device;
providing a separate processing device including a biometric capture module, a data capture module and a breathalyzer module;
seating said handheld wireless communication device within an interior cavity of said processing device wherein a touch screen display of said handheld communication device is accessible through a window in a housing of said processing device,
receiving control input from a user through said touch screen display of said handheld wireless communication device;
communicating said control input to a central processing unit of said processing device;
controlling said biometric capture module, said data capture module and said breathalyzer module responsive to said control input to capture biometric data, identification data and breath samples from person to be identified and create output data;
transferring output data to said wireless communication device;
communicating with a wireless communication network through a wireless communication transceiver,
communicating with a computer network connected to said wireless communication network,
transmitting said output data over said communication network to said computer network;
identifying said person based on said qualified image of said biometric attribute;
receiving identification data on said handheld wireless communication device responsive to said comparison; and
displaying said identification data on said touch screen display.

10. The method of claim 9 further comprising a second biometric capture module for capturing a second biometric attribute of said individual to be identified, said second biometric attribute comprising a fingerprint, said second biometric capture module comprising a fingerprint capture module.

11. The method of claim 9, wherein said wireless communication device includes a digital camera having a lens, said housing of said processing device having a camera window in communication with said interior cavity, said lens being located within said camera window of said housing when said wireless communication device is seated within said interior cavity.

12. The method of claim 9, wherein said data capture module is selected from the group consisting of: barcode scanner, smart card reader, magnetic stripe reader, machine reader zone (MRZ) reader, HID reader, RFID reader, and signature capture device.

* * * * *